United States Patent [19]

Alter et al.

[11] Patent Number: 4,919,652

[45] Date of Patent: Apr. 24, 1990

[54] SYRINGE

[75] Inventors: Konrad G. Alter, Maylands; Jennifer D. Griffiths, West Leederville, both of Australia

[73] Assignee: Nujenko Pty. Ltd., Welshpool, Australia

[21] Appl. No.: 263,705

[22] Filed: Oct. 28, 1988

[51] Int. Cl.⁵ .............................................. A61M 5/00
[52] U.S. Cl. .................................... 604/110; 604/195; 604/220
[58] Field of Search ............... 604/195, 198, 263, 110, 604/220, 218

[56] References Cited

U.S. PATENT DOCUMENTS 4,562,844 1/1986 Carpenter et al. ............... 604/220 X
4,747,830 5/1988 Gloyer et al. ........................ 604/110

Primary Examiner—John D. Yasko
Attorney, Agent, or Firm—Harness, Dickey & Pierce

[57] ABSTRACT

Several embodiments of disposable syringes having a barrel, a plunger and needle wherein the plunger is adapted to withdraw the needle and be permanently deformed so as to render the syringe incapable of a second use after an injection has been made.

15 Claims, 6 Drawing Sheets

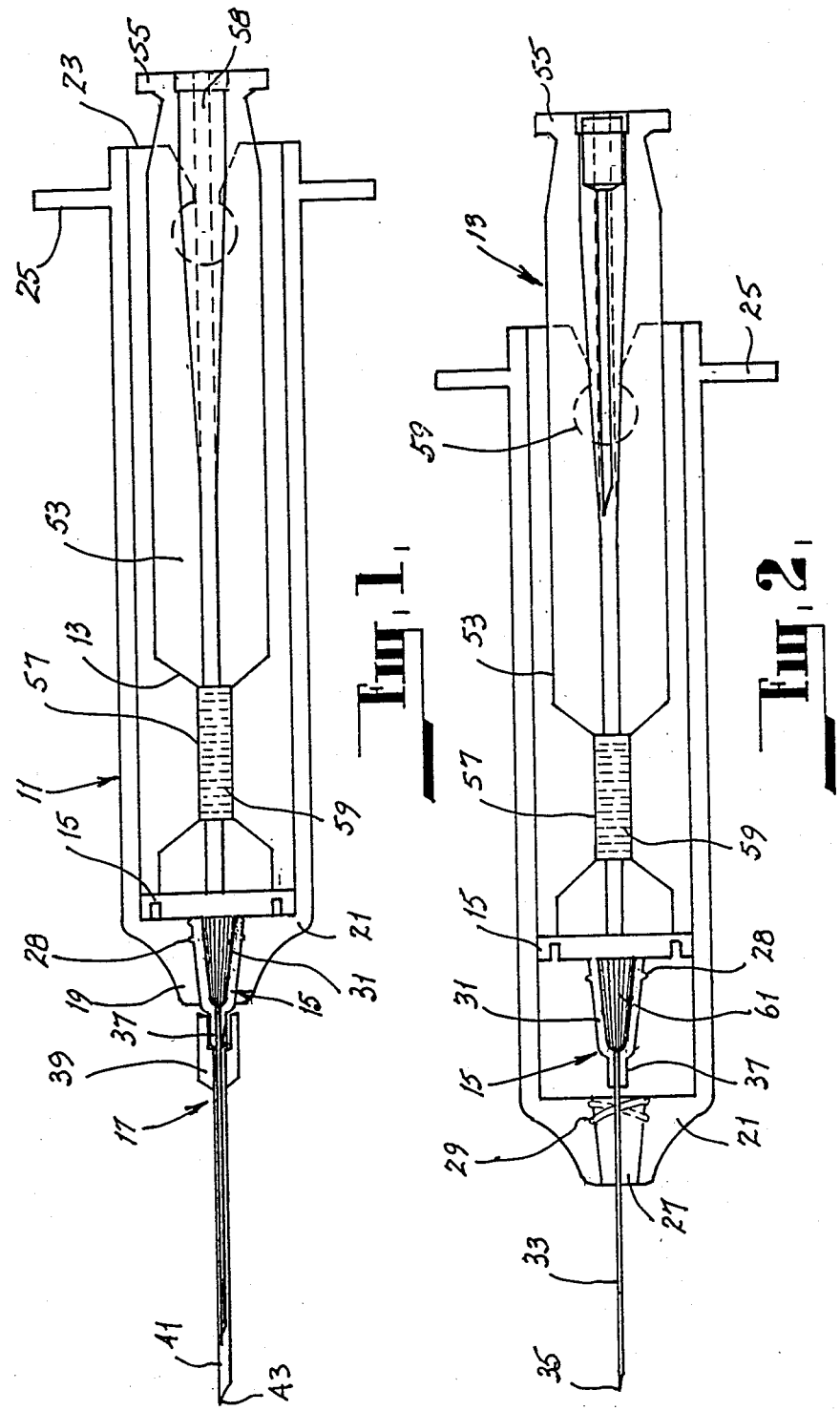

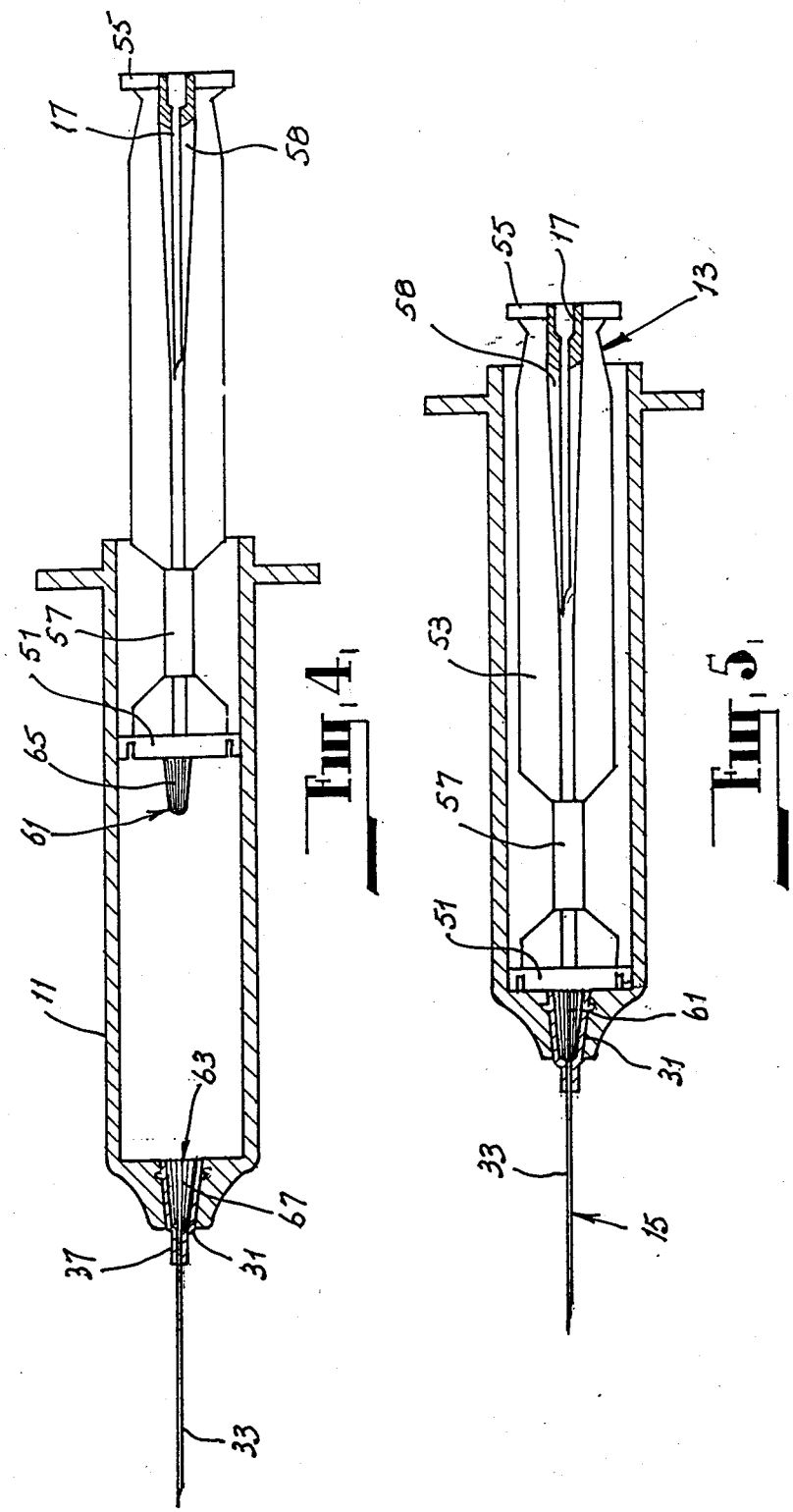

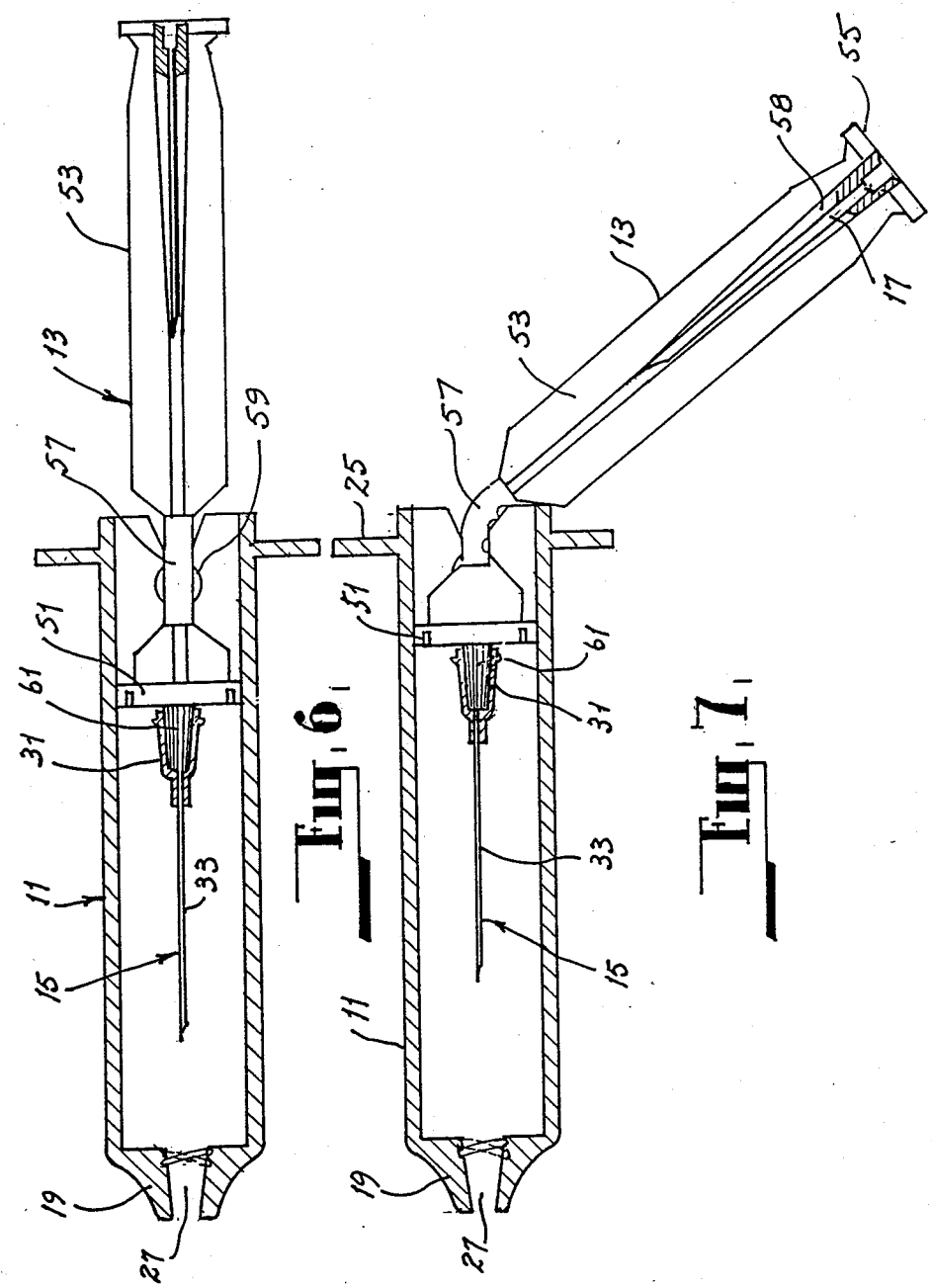

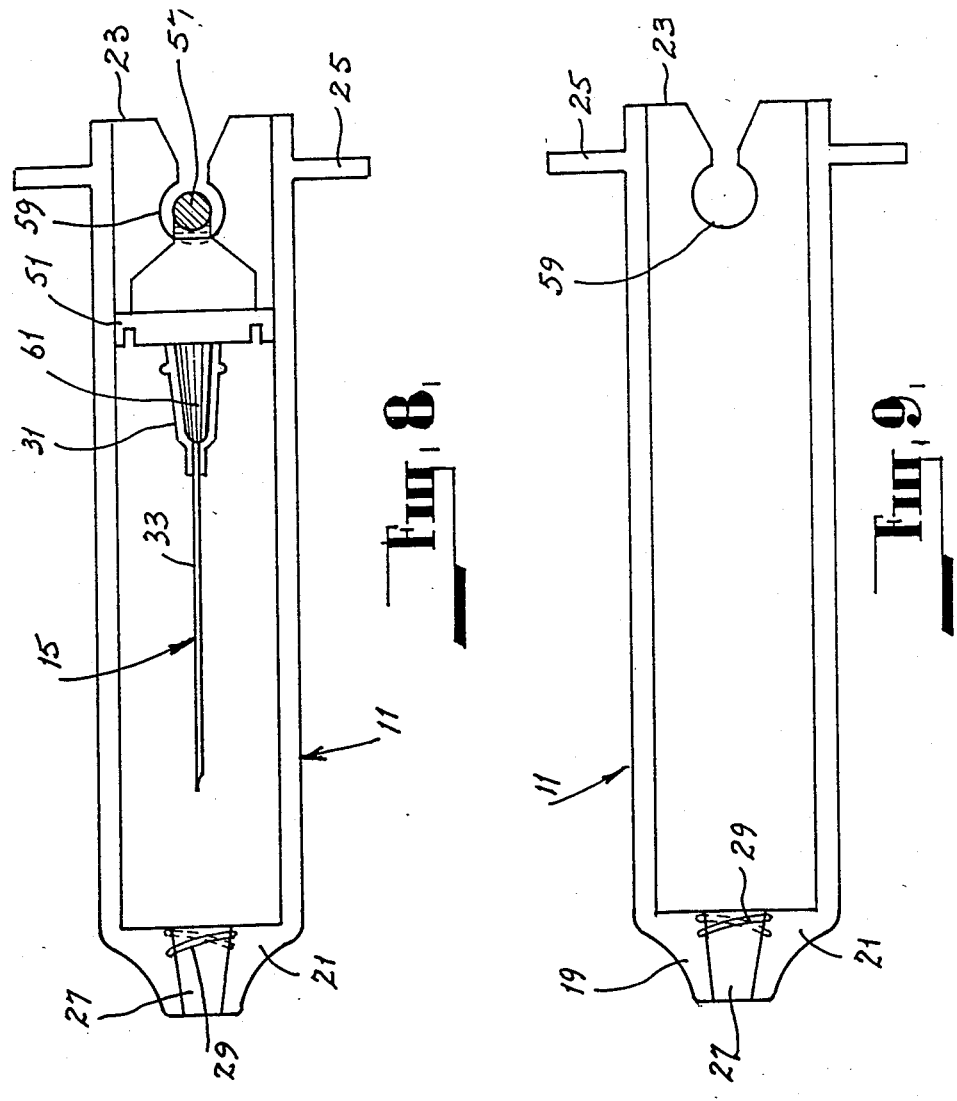

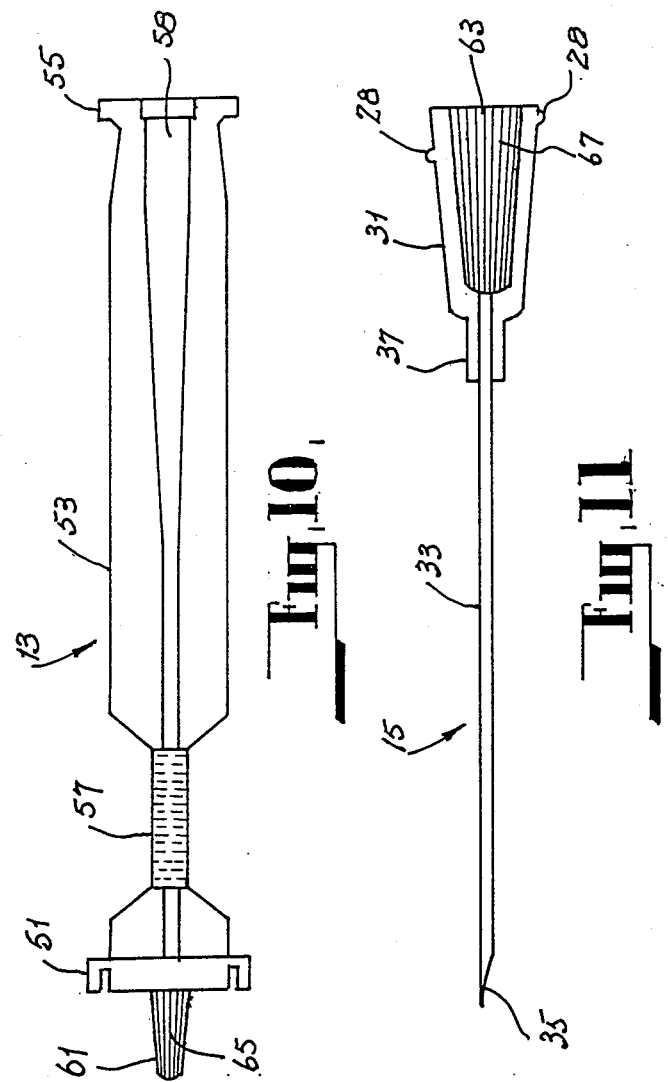

SYRINGE

BACKGROUND OF THE INVENTION

THIS INVENTION relates to syringes and more particularly syringes intended for single use only.

Throughout the specification the term "syringe" shall be taken to include a hypodermic syringes and other device incorporating a needle for injecting fluid into, or extracting fluid from, a body.

Syringes are commonly intended for single use only and disposal after such use, as any subsequent use carries with it the possibility of transmission of infection by the needle of the syringe. Nevertheless there are instances where single-use syringes are used again contrary to advice from health authorities, and there is a need for a syringe which can be used only once.

It is an object of this invention to provide a syringe which can be effectively rendered in inoperative after use.

SUMMARY OF THE INVENTION

In one form the invention resides in a syringe comprising a barrel, a plunger receivable in the barrel and movable therealong, the plunger including a shank, characterised in that the shank is selectively deformable to render the plunger inoperable.

Preferably the shank includes a weakened section at which it can be fractured to effect deformation of the shank.

Preferably, the weakened section of the shank is adapted to be fractured upon application of a predetermined bending force to the shank.

Conveniently, the weakened section is of reduced cross-sectional area in comparison to the remainder of the shank. Alternatively or additionally, the weakened section may include at least one cavity or other means for providing a zone of weakness in the weakened section.

Preferably, the barrel includes a side wall having an aperture opening onto an end of the barrel beyond which the shank extends, said aperture being adapted to receive a portion of the shank upon lateral deflection of the outer end portion of the shank during fracturing thereof.

Preferably, said portion of the shank receivable in said aperture is a portion of the weakened section of the shank.

Preferably, said aperture in the side wall of the barrel is configured to inhibit removal of the shank once it is received fully within the aperture.

In additional to preventing reuse of a syringe, it is beneficial to provide the syringe with a feature whereby the needle can be retracted into the barrel after use. The purpose of retracting the needle into the barrel is to ensure that a person handling the syringe is protected from inadvertent wounding by the contaminated needle. This reduces the likelihood of transmission of infection by a contaminated needle.

To this end, the syringe preferably comprises a needle portion having a base and a needle mounted on the base and projecting from the base, securing means for releasably securing the base of the needle portion to the barrel with the needle extending outwardly from the barrel and the bore in the needle communicating with the interior of the barrel, said securing means being arranged to effect release of said base from the barrel upon rotation of the base relative to the barrel, an engaging means for releasably engaging the plunger with said base whereby when so engaged with the base the plunger can be rotated to effect release of the base from the barrel and then be retracted to move the needle into the region within the barrel.

Preferably, the securing means comprises screw means for threadingly engaging the base to the barrel. The screw means preferably comprises a multiple thread.

The engaging means preferably comprises a socket provided on the base of the needle portion and a projection provided on the plunger for reception in the socket and engagement therewith.

Preferably, the socket is aligned with the needle so as to provide communication between the needle and the interior of the barrel.

Engagement between the socket and the projection is effected by pushing the plunger to insert the projection into the socket.

BRIEF DESCRIPTION OF THE DRAWINGS

The invention will be better understood by reference to the following description of one specific embodiment thereof as shown in the accompanying drawings in which:

FIG. 1 is a sectional view of a syringe according to the embodiment with the needle portion shown secured to the barrel;

FIG. 2 is a view similar to FIG. 1 except that the needle portion is shown detached from the barrel and partially retracted into the barrel;

FIG. 4 is a sectional elevational view of the syringe shown prior to injection of the fluid contained in the barrel;

FIG. 5 is a sectional elevational view of the syringe shown after injection of the fluid has been completed and prior to retraction of the needle into the barrel;

FIG. 6 is a sectional elevational view of the syringe shown after retraction of the needle into the barrel and prior to deformation of the shank of the plunger;

FIG. 7 is a view similar to FIG. 6 with the exception that the shank of the plunger is shown partially fractured;

FIG. 8 is a sectional elevational view of the syringe shown after fracturing of the shank (with the outer section of the shank shown removed for the purpose of clarity of illustration);

FIG. 9 is a sectional elevational view of the barrel of the syringe;

FIG. 10 is an elevational view of the plunger of the syringe; and

FIG. 11 is a partly sectioned elevational view of the needle portion of the syringe.

DETAILED DESCRIPTION OF THE PREFERRED EMBODIMENTS OF THE INVENTION

Figure 3:
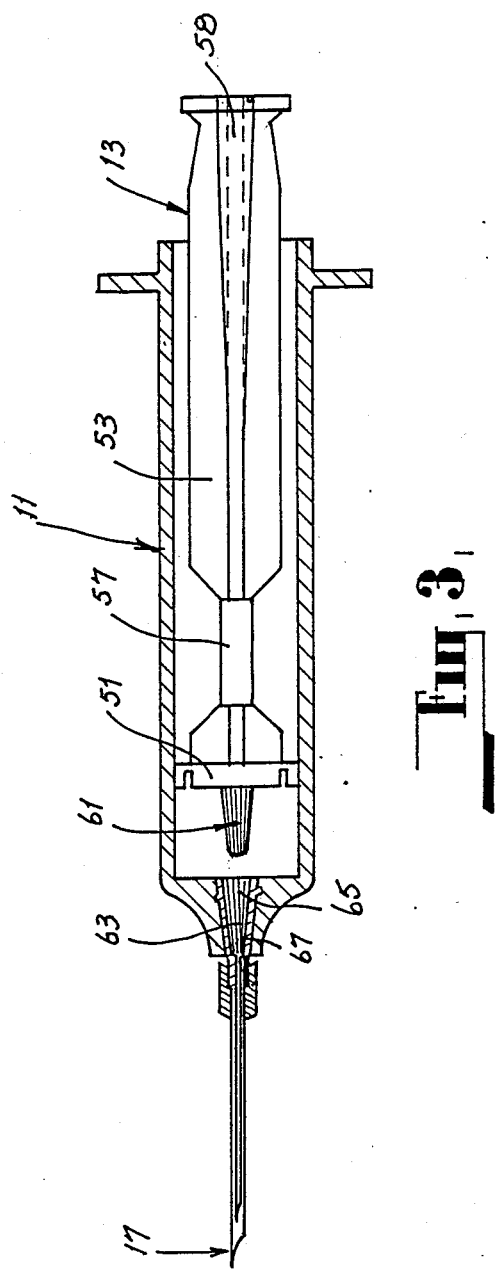
FIG. 3 is a sectional elevational view of the syringe shown during drawing of fluid into the barrel for injection into a patient at a later stage.

The embodiment shown in the drawings is directed to a hypodermic syringe intended for single use only and then disposal. The syringe comprises a syringe barrel 11, a plunger 13, a needle portion 15 and a filling needle portion 17.

The barrel 11 has a nozzle 19 at the distal end 21 thereof and is open at the proximal end 23. A flange 25 is formed around the opening at the proximal end 23 of the barrel to provide a means by which a user may grip the barrel while using the syringe. The nozzle 19 defines an axial passage 27 one end of which communicated with the interior of the barrel while the other end opens to the exterior of the barrel. An internal thread formation 29 comprising multiple threads is provided on the wall of the passage 27, the purpose of which will become apparent later.

The needle portion 15 is detachably mountable on the barrel. The needle portion includes a base 31 and a hollow needle 33 mounted onto the base. The needle 33 has a sharp-pointed end 35 opposite the base 11. The base 31 is adapted to be received within the axial passage 27 defined within the nozzle of the barrel and has protrusions 28 for threadingly engaging the internal thread formation 29 provided on the wall of the passage 27.

The base 31 is hollow and when engaged in position within the nozzle of the barrel provides for fluid communication between the hollow needle 33 and the interior of the barrel.

When the needle portion 15 is to be mounted onto the barrel 11, it is inserted into the barrel through the opening at the proximal end 23 and advanced along the barrel and into the axial passage 27 of the nozzle where the base can be threadedly engaged with the nozzle.

The base 31 is provided with a hub 37 which is adapted to receive the filling needle portion. The filling needle portion is intended to locate over the hollow needle 33 and is used to draw fluid out of a vial or other container and into the syringe. The filling needle portion includes a base 39 which is adapted for location on the hub 37 and a hollow needle 41 which can be received around the hollow needle 33. The hollow needle 41 has a sharp-pointed end 43 which extends beyond the sharp-pointed end 35 of the needle 33, as shown in the drawings. The filling needle portion 17 is fitted into position on the needle portion 15 when injection fluid is to be drawn into the syringe and is removed after the filling operation, the needle portion 15 being used in the injection stage. The purpose of the filling needle portion 17 is to be maintain the sterile state of the needle portion 15 during the filling operation.

The plunger 13 comprises a piston 51 and a shank 53. The piston 51 is received in the syringe barrel 11 and is in sliding and sealing engagement with the barrel. The shank 53 is connected to the piston 51 and extends out through the opening at the proximal end of the syringe barrel. The outer end of the shank 53 has a flange 55 to facilitate manual operation of the plunger.

The shank 53 is of a generally cruciform shape in cross-section except for a weakened section 57 at a region along the length of the shank. In the illustrated embodiment, the weakened section is located towards the piston end of the shank. The weakened section 57 is of reduced width in relation to the remainder of the shank and is provided with recesses 59 in its surface to enhance its weakened condition. The purpose of the weakened section 57 is to allow the shank to be fractured upon the application of a bending force to it. Fracturing of the shank effectively renders the plunger inoperable.

A cavity 58 is provided in the shank and opens onto the free end thereof for storage of the filling needle portion 17 after use.

An aperture 60 as provided in the side wall of the syringe barrel 11 and opens onto the proximal end 23 of the syringe barrel. The purpose of the aperture 60 is to receive portion of the weakened section 57 of the shank 53 upon lateral deflection of the shank as it is being fractured. The aperture is of a configuration which inhibits removal of the shank from the aperture once received fully therein; in this embodiment such configuration is of generally keyhole shape.

It is preferably, although not essential, that the weakened section 57 of the shank be constructed such that the shank remains intact after fracturing rather than separating into pieces, as this avoids the need to dispose of the separate pieces. It will be noted that FIG. 8 of the drawings shows the outer portion of the shank removed; this has been done for the sole purpose of illustrating the weakened section 57 received within the aperture 59 and is not intended to indicate that the shank separates into pieces at the weakened section.

The face of the piston opposite the shank is provided with an axial projection 61 adapted for reception in a socket 63 defined within the hollow base 31 of the needle portion 15. The axial projection 61 is of generally conical form and the socket 63 is of complementary shape to snugly receive the projection. The tapered surfaces of the projection 61 and the socket 63 are provided with splines 65 and 67 respectively which mesh when the projection 61 is received within the socket 63. With the projection 61 received in the socket 63, rotational torque produced by rotating the plunger about its longitudinal axis is transmitted through the projection and socket to the base 31 of the needle portion. The rotational torque transmitted to the base 31 of the needle portion effects rotation of the base to unscrew the needle portion from the nozzle. Once the needle portion has been unscrewed from the nozzle, withdrawal of the plunger retracts the needle portion into the barrel.

Operation of the syringe will now be described in relation to FIGS. 3 to 8 of the accompanying drawings. Fluid for injection into the body of a patient is drawn into the syringe with the filling needle portion 17 in position, by retracting the plunger 13, as shown in FIG. 3. The filling needle portion is then removed from around the needle portion 15 and stored in the cavity 58 within the free end of the shank. The syringe is at this stage in readiness for injection of the fluid previously drawn into the barrel, as shown in FIG. 4. The needle 33 is inserted into the body of the patient and the plunger pushed inwardly thereby to force the injection fluid through the hollow base 31 and needle 33 into the body of the patient. As the piston 51 approaches the distal end of the syringe barrel 11 towards the end of the injection stage, the projection 61 enters the socket 63. By the end of the injection stage, the projection is snugly received in the socket, as shown in FIG. 5. The plunger is then rotated in the direction appropriate to unscrew the protrusions 28 on the base 31 from the thread formation 29 in the nozzle. After the base has been unscrewed from the nozzle, the plunger (which remain connected to the base of the needle portion) is retracted to withdraw the needle portion 15 into the syringe barrel, as shown in FIG. 6. The plunger is then positioned such that the weakened section 57 of the shank 53 is located adjacent the aperture 60 in the syringe barrel and a bending force is applied to the shank in the direction towards the aperture, as shown in FIG. 7. The resulting lateral deflection of the shank causes the weakened section to fracture and enter the aperture, as shown in FIG. 8. The keyhole shape of the aperture serves to inhibit removal of the shank from the aperture and so the plunger is effectively locked to the syringe barrel, with the needle 33 being confined within the barrel where it is not exposed for inadvertent puncturing of the patient or any person handling the syringe.

Because the shank of the plunger has been fractured, the syringe cannot be readily used again and thus the possibility of transmission of infection by the contaminated needle is avoided.

It should be appreciated that the scope of the invention is not limited to the scope of the embodiment described.

We claim:

1. A syringe comprising a barrel, a plunger receivable in the barrel and movable therealong, the plunger including a shank, said shank having a selectively deformable portion for rendering said plunger inoperable, and said barrel including a side wall having an aperture opening onto an end of the barrel beyond which the shank extends, said aperture being adapted to receive said deformable portion of said shank upon lateral deflection of the outer end portion of said shank during deformation.

2. A syringe according to claim 1 wherein the shank includes a weakened section at an end of said deformable portion which it can be fractured upon deformation of the shank.

3. A syringe according to claim 2 wherein the weakened section of the shank is adapted to be fractured upon application of a predetermined bending force to the shank.

4. A syringe according to claim 2 wherein the weakened section is of reduced cross-sectional area in comparison to the remainder of the shank.

5. A syringe according to claim 2, wherein the weakened section includes at least one cavity or other means for providing a zone of weakness in the weakened section.

6. A syringe according to claim 2 wherein said portion of the shank receivable in said aperture is a portion of the weakened section of the shank.

7. A syringe according to claim 1 wherein said aperture in the side wall of the barrel is configured to inhibit removal of the shank once it is received fully within the aperture.

8. A syringe according to claim 7 wherein the aperture is of generally keyhole shape.

9. A syringe according to claim 1 further comprising a needle portion having a base and a needle mounted on the base and projecting from the base, securing means for releasably securing the base of the needle portion to the barrel with the needle extending outwardly from the barrel and the bore in the needle communicating with the interior of the barrel, said securing means being arranged to effect release of said base from the barrel upon rotation of the base relative to the barrel, and engaging means for releasably engaging the plunger with said base whereby when so engaged with the base the plunger can be rotated to effect release of the base from the barrel and then be retracted to move the needle into the region within the barrel.

10. A syringe according to claim 9 wherein the securing means comprises screw means for threadingly engaging the base to the barrel.

11. A syringe according to claim 9 wherein the engaging means comprises a socket provided on the base of the needle portion and a projection provided on the plunger for reception in the socket and engagement therewith.

12. A syringe according to claim 11 wherein the socket is aligned with the needle so as to provide communication between the needle and the interior of the barrel.

13. A syringe according to claim 3 wherein the weakened section is of reduced cross-sectional area in comparison to the remainder of the shank.

14. A syringe according to claim 4 wherein the weakened section includes at least one cavity or other means for providing a zone of weakness in the weakened section.

15. A syringe according to claim 3 wherein the weakened section includes at least one cavity or other means for providing a zone of weakness in the weakened section.

* * * * *